(12) United States Patent
Laursen et al.

(10) Patent No.: US 6,281,336 B1
(45) Date of Patent: Aug. 28, 2001

(54) PROCESS FOR PRODUCING IMMUNOGLOBULINS FOR INTRAVENOUS ADMINISTRATION AND OTHER IMMUNOGLOBULIN PRODUCTS

(75) Inventors: Inga Laursen, Hellerup; Børge Teisner, Odense C, both of (DK)

(73) Assignee: Statens Serum Institut, Copenhagen S. (DK)

( * ) Notice: Subject to any disclaimer, the term of this patent is extended or adjusted under 35 U.S.C. 154(b) by 0 days.

(21) Appl. No.: 09/328,497

(22) Filed: Jun. 9, 1999

Related U.S. Application Data

(60) Provisional application No. 60/102,055, filed on Sep. 28, 1998.

(30) Foreign Application Priority Data

Jun. 9, 1998 (EP) ................................................ 98201909

(51) Int. Cl.$^7$ .......................... A61K 39/395; C07K 16/00
(52) U.S. Cl. ..................... 530/390.1; 424/176.1; 424/177.1; 530/390.5; 530/414; 530/416; 530/417; 530/420; 530/421
(58) Field of Search ............... 424/176.1, 177.1; 530/390.1, 390.5, 414, 416, 417, 420, 421

(56) References Cited

U.S. PATENT DOCUMENTS

| | | | |
|---|---|---|---|
| 3,869,436 | * 3/1975 | Falksveden | 530/390.5 |
| 4,272,521 | * 6/1981 | Zuffi | 530/390.5 |
| 4,314,997 | 2/1982 | Shandrom | 514/2 |
| 4,315,919 | 2/1982 | Shanbrom | 514/1 |
| 4,764,369 | 8/1988 | Neurath et al. | 424/176.1 |
| 4,876,088 | * 10/1989 | Hirao et al. | 424/177.1 |
| 4,880,913 | * 11/1989 | Doleschel et al. | 530/390.5 |
| 5,164,487 | * 11/1992 | Kothe et al. | 530/390.5 |
| 5,177,194 | * 1/1993 | Sarno et al. | 530/412 |
| 5,886,154 | * 11/1999 | Lebing et al. | 530/390.1 |

FOREIGN PATENT DOCUMENTS

| | | |
|---|---|---|
| 2364792 | 7/1974 | (DE) . |
| 0530447 | 10/1997 | (EP) . |
| WO8606727 | 11/1986 | (WO) . |
| WO 98/05686 | 2/1998 | (WO) . |

OTHER PUBLICATIONS

J Food Sci 58(6) 1993, 1282–90, Fichtali, et al. "Purification of antibodies . . . ".
J Am Chem Soc 68, 1946, 459–75, Cohn, et al. "Preparation and properties . . . ".
J Am Chem Soc 71, 1949, 541–50, Oncley, et al "Separation of antibodies . . . ".
Vox Sang 7, 1962, 414–24, Kistler et al, "Large scale production . . . ".
Biochem Biophys Acta 82, 1964, 463–75 Polson et al, "Fractionation of protein."
Vox Sang 23, 1972, 107–18, Polson et al., "Fractionation of plasma . . . ".
Blood Separation and Plasma Fractionation, 1991, WileyLiss, New York, p 266, Harns, J. (Ed.), Figure 3.
Anal Biochem 10, 1965, 358–61, Laurell, "Antigen–antibody crossed . . . ".

* cited by examiner

*Primary Examiner*—David Saunders
(74) *Attorney, Agent, or Firm*—Birch, Stewart, Kolasch & Birch, LLP

(57) ABSTRACT

The present invention relates to a process for purifying immunoglobulin G from a crude immunoglobulin-containing plasma protein fraction. Said process includes a number of steps of which the anion exchange chromatography and the cation exchange chromatography are preferably connected in series. An acetate buffer having a pH of about 5.0–6.0 and having a molarity of about 5–25 mM is preferably used throughout the purification process. The invention further comprises an immunoglobulin product which is obtainable by this process. The invention also relates to an immunoglobulin product which has a purity of more than 98%, has a content of IgG monomers and dimers of more than 98.5%, has a content of IgA less than 4 mg of IgA/l, and contains less than 0.5% polymers and aggregates. Said product does not comprise detergent, PEG or albumin as a stabilizer. The product is stable, virus-safe, liquid and ready for instant intravenous administration.

14 Claims, No Drawings

PROCESS FOR PRODUCING IMMUNOGLOBULINS FOR INTRAVENOUS ADMINISTRATION AND OTHER IMMUNOGLOBULIN PRODUCTS

This application claims priority on provisional Application No. 60/102,055 filed on Sep. 28, 1998, the entire contents of which are hereby incorporated by reference.

FIELD OF THE INVENTION

The present invention relates to a process for purifying immunoglobulins, i.e. immunoglobulin G (IgG), from crude plasma or from a crude plasma protein fraction. The invention also relates to an immunoglobulin product and to the use of such an immunoglobulin product for medical purposes.

BACKGROUND OF THE INVENTION

Human normal immunoglobulin (HNI) for use in the prevention and treatment of a number of infectious diseases was introduced in the late 1940's. HNI prepared by the cold ethanol fractionation method according to Cohn & Oncley (Cohn E., et al., (1946), J Am Chem Soc, 68, 459–475), (Oncley et al., (1949), J Am Chem Soc, 71, 541–550) and subsequently also by the modification made by Kistler and Nitschmann (Kistler P and Nitschmann HS, (1952), Vox Sang, 7, 414–424) proved to be both efficient and safe against the transmission of virus infection when administered subcutaneously or intramuscularly.

Congenital or acquired total or partial lack of immunoglobulin (primary and secondary immunodeficiency syndrome, respectively) manifests itself through frequent ordinary and serious infections, especially of a bacterial nature. The prevention of such infections was previously achieved by repeated intramuscular or subcutaneous injections of large amounts of HNI for up to several times a week as a life-lasting treatment, which is very painful when the medicament is given intramuscularly.

In the early sixties, administration of HNI by the intravenous route was therefore attempted. Trials showed that about 5% of healthy volunteers and about 95% of patients with an immunoglobulin deficiency developed immediate adverse effects varying from dyspnoea to circulatory shock and being of such serious nature that the intravenous administration of HNI had to be abandoned.

The reason for the adverse effects mentioned above turned out to be aggregates of immunoglobulins which, among other effects, strongly activated the complement system. This was in particular seen in patients lacking immunoglobulins. Especially serious adverse effects of an anaphylactic nature could be seen in patients who developed antibodies to IgA. Consequently, methods of avoiding aggregate formation and/or eliminating these aggregates during the preparation process were developed, and some twenty years ago the first generation of an immunoglobulin for intravenous administration (IVIG) was tested and found suitable.

The original purpose of an IVIG was to alleviate infectious episodes in patients with a congenital or acquired total or partial lack of immunoglobulins and to eliminate discomfort in connection with the administration of HNI. Another advantage of IVIG is that large doses of immunoglobulin can be given within a short time, and by this it is possible to obtain sufficiently high blood concentrations very quickly. Especially when treating serious bacterial infections it is of importance to establish high concentrations at sites of infections quickly.

In recent years, IVIG has furthermore proved to be efficient in other serious diseases, the treatment of which can otherwise be difficult, e.g. haemorrhages caused by the disappearance of the blood platelets on an immunological basis, idiopathic thrombocytopenic purpura (ITP), in some rare diseases such as Kawasaki's syndrome and a number of autoimmune diseases such as polyradiculitis (Guillain Barré's syndrome). Other diseases the treatment of which has been difficult to the present day are currently being subjected to clinical trials with IVIG. The mechanism of action in these diseases has only partly been clarified. The effect is supposed to be related to so-called immunomodulating properties of IgG, e.g. a blockage of Fcγ-receptors on phagocytic cells, increased metabolism of IgG, downregulation of the production of cytokines, and interference with a supposed network of idiotypes/anti-idiotypes, especially relevant for the neutralization of autoimmune reactivity.

The first generation of IVIG was prepared by pepsin cleavage of the starting material (Cohn fraction II), the purpose of the cleavage being removal of immunoglobulin aggregates. No column chromatography steps were included in the process. The product had to be freeze-dried in order to remain stable for a reasonable period of time and was dissolved immediately prior to use.

The starting material for the IVIG was HNI which had proved to be safe with respect to the transmission of viruses when used for intramuscular injection. Hence, IVIG was considered to be just as safe. After several years of clinical use, however, IVIG products from some manufacturers were surprisingly shown to cause transfer of hepatitis C virus infection.

Studies to elucidate the fate of viruses during the production of HNI showed that the removal of virus in the fractionation process from plasma to HNI is modest. The safety of HNI for intramuscular use is likely to be due to the fact that it contains protective immunoglobulins. In combination with the modest volume injected and the intramuscular route of administration, these protective immunoglobulins can neutralize and render common viruses in plasma non-infectious. Especially when large doses of immunoglobulin are given intravenously, virus infections may occur as demonstrated in the early 1990's. Therefore, it was recognized that the production processes should comprise one or more well-defined virus-inactivation and/or removal steps.

A second generation of IVIG based on uncleaved and unmodified immunoglobulin molecules with low anti-complementary activity and higher stability was introduced in the mid-eighties, but still in the form of a freeze-dried product. This IVIG was purified by several chromatography steps. Products of that kind presently dominate the market for IVIG. The first and second generations of IVIG thus appear as freeze-dried powders which are dissolved immediately prior to use.

Dissolution of freeze-dried IVIG is slow (up to 30 minutes for one vial). Several portions often have to be dissolved for one patient. As it is of high priority for the users to have an IVIG in a solution ready for use, liquid products have been introduced on the market. More importantly, there is still a need for improvement of the production process in order to obtain a highly purified, stable and fully native IVIG preparation with higher clinical efficacy and less adverse drug reactions. A further developed and improved process for purifying IgG from crude plasma or a plasma protein fraction for a virus-safe, liquid IVIG product is thus needed. Finally, the process should be designed in such a way that it can be used in a large scale production.

The purification process described in the present application leads to a liquid immunoglobulin product for intravenous administration which can be characterized as a highly purified, fully native, biologically active, double virus-inactivated, and stable new generation of IVIG, which does not contain any detergent, polyethylene glycol (PEG) or albumin as a stabilizer.

SUMMARY OF THE INVENTION

The present invention relates to an improved purification procedure and an improved liquid immunoglobulin product which, inter alia, can be administered intravenously.

An immunoglobulin product obtained by the method of the present invention could be called a third generation IVIG. The process is characterized by the following conditions for fractionation: pepsin cleavage is avoided, aggregates and particles are removed by precipitation (a process step validated to function as a virus removal step), further purification is achieved by column chromatographic ion exchange methods, S/D treatment is introduced as a virus-inactivating step, and the preparation is formulated as a liquid product.

Due to the improved purity of the immunoglobulin product obtainable by the process of the invention as compared to the prior art products, the addition of stabilizers such as a non-ionic detergent, PEG or albumin is not necessary in order to avoid aggregation of IgG during storage of the IVIG as a liquid product. The product obtainable by the process of the invention has a higher quality than the prior art products and provides improved clinical effects, and unwanted adverse effects are virtually absent.

DETAILED DISCLOSURE OF THE INVENTION

The present invention relates to a process for purifying immunoglobulins, i.e. IgG, from crude plasma or an immunoglobulin-containing plasma protein fraction, which process comprises the steps of:

(a) preparing an aqueous suspension of the crude immunoglobulin-containing plasma protein fraction;

(b) adding a water soluble, substantially non-denaturating protein precipitant to said suspension of step (a) in an amount sufficient to cause precipitation of a high proportion of non-immunoglobulin G proteins, aggregated immunoglobulins and particles including potentially infectious particles such as virus particles, without causing substantial precipitation of monomeric immunoglobulin G, thereby forming a mixture of a solid precipitate and a liquid supernatant;

(c) recovering a clarified immunoglobulin G-containing supernatant from the mixture of step (b);

(d) applying the clarified immunoglobulin G-containing supernatant of step (c) to an anion exchange resin and subsequently a cation exchange resin;

(e) washing out protein contaminants and the protein precipitant from the cation exchange resin with a buffer having a pH and ionic strength sufficient to remove the contaminants from the resin without causing substantial elution of immunoglobulin G;

(f) eluting immunoglobulin G from the cation exchange resin with a substantially non-denaturating buffer having a pH value and ionic strength sufficient to cause efficient elution of the immunoglobulin G, thereby recovering an immunoglobulin G-containing eluate;

(g) performing a dia/ultrafiltration on the immunoglobulin G-containing eluate of step (f) to concentrate and/or dialyse the eluate and optionally adding a stabilizing agent (h) adding a virucidal amount of virus-inactivating agent to the immunoglobulin G-containing dia/ultrafiltrated and optionally stabilized fraction of step (g) resulting in a substantially virus-safe immunoglobulin G-containing solution;

(i) applying the immunoglobulin G-containing solution of step (h) to an anion exchange resin and subsequently to a cation exchange resin;

(j) washing the cation exchange resin of step (i) with a buffer having a pH and ionic strength sufficient to wash out the protein contaminants and the virus-inactivating agent from the resin without causing substantial elution of immunoglobulin G;

(k) eluting immunoglobulin G from the cation exchange resin of step (j) with a substantially non-denaturating buffer having a pH and ionic strength sufficient to cause efficient elution of the immunoglobulin G, thereby recovering an immunoglobulin G-containing eluate; and (l) subjecting the immunoglobulin G-containing eluate of step (k) to dia/ultrafiltration to lower the ionic strength and concentrate the immunoglobulin G of the solution, and adjusting the osmolality by adding a saccharide.

The starting material of the present purification process can be crude plasma, but is advantageously an immunoglobulin-containing crude plasma protein fraction. The starting material for the purification process can be normal human plasma or may originate from donors with high titers of specific antibodies, e.g. hyperimmune plasma. In the present specification, the term "immunoglobulin-containing plasma fraction" is to encompass all possible starting materials for the present process, e.g. cryoprecipitate-free plasma or cryoprecipitate-free plasma from which various plasma proteins, such as Factor IX and Antithrombin, have been removed, different Cohn fractions, and fractions obtained through precipitation procedures by PEG (Poison et al., (1964), Biochem Biophys Acta, 82, 463–475; Poison and Ruiz-Bravo, (1972) Vox Sang, 23, 107–118) or by ammonium sulphate. In a preferred embodiment, the plasma protein fraction is Cohn fractions II and III, but Cohn fraction II, or Cohn fractions I, II and III can be used as well. The different Cohn fractions are preferably prepared from plasma by a standard Cohn-fractionation method essentially as modified by Kistler-Nitschmann. In addition to immunoglobulins, the Cohn fractions contain e.g. fibrinogen, α-globulins and β-globulins, including various lipoproteins, which should preferably be removed during the subsequent purification process. Filter aid may or may not be present depending on the isolation method used to obtain the Cohn fractions (i.e. centrifugation or filtration).

The first step of the process according to the invention involves preparing an aqueous suspension of an immunoglobulin-containing plasma protein fraction, wherein the IgG concentration in the suspension is sufficiently high so that, during the following precipitation step, a major proportion of the non-IgG-proteins, especially those of higher molecular weight, the aggregated immunoglobulins and other aggregated proteins as well as potentially infectious particles precipitate without substantial precipitation of monomeric IgG. This is generally achieved if the concentration of the IgG in the buffered and filtered suspension is at least about 4 g/l before the addition of the precipitant. It should be taken into consideration that the influence of the protein concentration as well as pH and temperature of the suspension on the precipitation depends on the precipitant chosen.

It is preferred that the plasma protein fraction is suspended in water and/or buffer at a substantially non-denaturating temperature and pH. The term "substantially non-denaturating" implies that the condition to which the term refers does not cause substantial irreversible loss of functional activity of the IgG molecules, e.g. loss of antigen binding activity and/or loss of biological Fc-function (see Example 2).

Advantageously, the plasma protein fraction is suspended in water acidified with at least one non-denaturating buffer system at volumes of from 6 to 9, preferably from 7 to 8, times that of the plasma protein fraction. The pH of the immunoglobulin-containing suspension is preferably maintained at a pH below 6, such as within the range of 4.0–6.0, preferably 5.1–5.7, most preferably about 5.4, in order to ensure optimal solubility of the immunoglobulin and to ensure optimal effect of the subsequent PEG precipitation step. Any suitable acidic buffer can be used, but the buffer system preferably contains at least one of the following buffers and acids: sodium phosphate, sodium acetate, acetic acid, HCl. Persons skilled in the art will appreciate that numerous other buffers can be used.

The immunoglobulin suspension is preferably maintained at a cold temperature, inter alia in order to prevent substantial protein denaturation and to minimize protease activity. The immunoglobulin suspension and water as well as the buffer system added preferably have the same temperature within the range of 0–12° C., preferably 0–8° C., most preferably 1–4° C.

The suspension of an ethanol precipitated paste contains relatively large amounts of aggregated protein material. Optionally, the immunoglobulin-containing suspension is filtered in order to remove e.g. large aggregates, filter aid, if present, and residual non-dissolved paste. The filtration is preferably performed by means of depth filters, e.g. C150 AF, AF 2000 or AF 1000 (Schenk), 30LA (Cuno) or similar filters. The removal of aggregates, filter aid, if present, and residual non-dissolved protein material could also be carried out by centrifugation.

At least one water-soluble, substantially non-denaturating protein precipitant is added to the immunoglobulin-containing filtered suspension in an amount sufficient to cause precipitation of a high proportion of high molecular weight proteins, lipoproteins, aggregated proteins, among these aggregated immunoglobulins. Other particulate material, such as potentially infectious particles, e.g. virus particles, are also precipitated without causing substantial precipitation of monomeric IgG. The term "infectious particles" in the present context comprises e.g. virus particles (such as hepatitis viruses, HIV1 and HIV2) and bacteria.

Substantially non-denaturating, water-soluble protein precipitants are well known in the field of protein purification. Such precipitants are used for protein fractionation, resulting in partial purification of proteins from suspensions. Suitable protein precipitants for use in the process of the present invention include various molecular weight forms of PEG, caprylic acid, and ammonium sulphate. Those skilled in the art will appreciate that several other non-denaturating water soluble precipitants may be used as alternative means for the precipitation. The term "adding a protein precipitant" and variants of that term implies the addition of one or more types of protein precipitation agents.

A preferred precipitant is the organic agent PEG, particularly PEG within the molecular weight range of 3000–8000 Da, such as PEG 3350, PEG 4000, PEG 5000, and especially PEG 6000 (the numbers of these specific PEG compounds represent their average molecular weight). The advantage of using PEG as a precipitant is that PEG is non-ionic and has protein stabilizing properties, e.g. PEG in low concentration is well known as a stabilizer of IVIG products. The precipitation step also functions as a virus-removal step. PEG concentrates and precipitates the viruses irrespective of the species, size, and surface coating of these.

A given amount of protein precipitant is added to the filtrated suspension to precipitate the majority of high molecular weight and aggregated proteins and particles, without a substantial precipitation of monomeric IgG, forming a clear supernatant solution. The protein precipitant may be added as a solid powder or a concentrated solution.

For PEG as precipitant a general rule applies that the higher the molecular weight of the compound, the lower the concentration of PEG is needed to cause protein to precipitate. When PEG 3350, PEG 4000 or preferably PEG 6000 is used, the concentration of the precipitant in the filtrated suspension is advantageously within the range of 3–15% by weight, such as 4–10% (such as about 5%, 6%, 7%, 8%, 9%, 10%), wherein 6% is most preferred. In the precipitation step, the precipitation process is allowed to proceed at least until equilibrium is reached between the solid and the liquid phase, e.g. usually for at least two hours, such as from about 2 hours to about 12 hours, preferably about 4 hours. Throughout the precipitation the suspension is preferably maintained at a low temperature (e.g. less than about 12° C., such as less than about 10° C., preferably between 2° C. and 8° C.). The most suitable temperature depends on the identity of the protein precipitant.

After completion of the protein precipitation, a clarified supernatant containing IgG almost exclusively in a monomeric form is recovered from the mixture of solid precipitate and liquid supernatant resulting from the precipitation. The recovery can be performed by conventional techniques for separating liquid from solid phase, such as centrifugation and/or filtration. Preferably, a flow-through centrifuge (e.g. Westfalia) with 1000–5000 g force is used.

Optionally, the recovered, clarified, IgG-containing supernatant is depth filtered to remove larger particles and aggregates. This is optionally followed by sterile filtration performed by use of a conventional sterilization filter (such as a 0.22 μm filter from Millipore or Sartorius), which eliminates e.g. bacteria from the solution.

The clarified and optionally filtrated IgG-containing supernatant is subjected to at least one step, such as two steps, but optionally more steps of anion and cation exchange chromatography in order to remove a substantial proportion of the remaining non-IgG contaminants, e.g. IgA, albumin as well as aggregates. In a preferred embodiment, the clarified and optionally filtrated IgG-containing supernatant is applied to an anion exchange resin and subsequently a cation exchange resin packed in two columns of appropriate dimensions.

When performing the ion exchange chromatography steps for the purification of IgG, it is preferred that the conditions, e.g. the pH and ionic strength, are chosen in such a way that a major portion of the contaminants (e.g. non-IgG proteins such as IgA, transferrin, albumin, and aggregates) in the applied solution binds to the anion exchange resin, whereas substantially no IgG adsorbs to the anion exchange resin. With respect to the subsequent cation exchange chromatography, the preferred conditions chosen result in binding of substantially all of the IgG molecules present in the solution applied to the cation exchange resin. Protein contaminants not adsorbed to the anion exchange resin and the precipitation agent are removed in the subsequent washing of the cation exchange resin.

In a preferred embodiment of the present process, the anion exchange resin and the cation exchange resin are connected in series. In the present context, the term "connected in series", when used in connection with the ion exchange resins, means that the proteins passing through the anion exchange resin are loaded directly onto the cation exchange resin with no change of buffer or other conditions.

Several reasons make it advantageous that the anion exchange and cation exchange chromatography is carried out in one step using two serially connected chromatography columns, instead of two independent chromatography steps, e.g. with different buffer compositions. The use of two serially connected chromatography columns makes the operation more practical, e.g. there is no need for an intermediary step of collecting the IgG-containing fraction between the two ion exchange chromatographic methods, for possibly adjusting pH and ionic strength. In addition the buffer flow is applied to both of the columns at the same time, and the two columns are equilibrated with the same buffer. However, it is contemplated that it is also possible to perform the chromatography step in two steps, i.e. the anion exchange resin and cation exchange resin are not connected in series. Performing the chromatography in two steps would though, as mentioned above, be more laborious compared to keeping the ion exchange resins connected in series.

It is presently contemplated that the high degree of purity, the high content of IgG monomers and dimers and the low content of IgA in the IVIG product of the invention are partly due to the use of two serially connected chromatography columns.

As will be known by the person skilled in the art, ion exchangers may be based on various materials with respect to the matrix as well as to the attached charged groups. For example, the following matrices may be used, in which the materials mentioned may be more or less crosslinked: agarose based (such as Sepharose CL-6B®, Sepharose Fast Flow® and Sepharose High Performance®), cellulose based (such as DEAE Sephacel®), dextran based (such as Sephadex®), silica based and synthetic polymer based. For the anion exchange resin, the charged groups which are covalently attached to the matrix may e.g. be diethylaminoethyl (DEAE), quaternary aminoethyl (QAE), and/or quaternary ammonium (Q). For the cation exchange resin, the charged groups which are covalently attached to the matrix may e.g. be carboxymethyl (CM), sulphopropyl (SP) and/or methyl sulphonate (S). In a preferred embodiment of the present process, the anion exchange resin employed is DEAE Sepharose Fast Flow®, but other anion exchangers can be used. A preferred cation exchange resin is CM Sepharose Fast Flow®, but other cation exchangers can be used.

The appropriate volume of resin used when packed into an ion exchange chromatography column is reflected by the dimensions of the column, i.e. the diameter of the column and the height of the resin, and varies depending on e.g. the amount of IgG in the applied solution and the binding capacity of the resin used.

Before performing an ion exchange chromatography, the ion exchange resin is preferably equilibrated with a buffer which allows the resin to bind its counterions. Preferably, the anion and cation exchange resins are equilibrated with the same buffer, as this facilitates the process since then only one buffer has to be made and used.

If, for instance, the chosen anion exchange resin is DEAE Sepharose FF® and the cation exchange resin CM Sepharose FF® and the columns are connected in series, then the columns are advantageously both equilibrated with a non-denaturating acidic buffer having about the same pH and ionic strength as the IgG solution to be loaded. Any of a variety of buffers are suitable for the equilibration of the ion exchange columns, e.g. sodium acetate, sodium phosphate, tris(hydroxymethyl)amino-methane. Persons skilled in the art will appreciate that numerous other buffers may be used for the equilibration as long as the pH and conductivity are about the same as for the applied IgG solution. A preferred buffer for the equilibration of the anion exchange column and cation exchange column when connected in series is a sodium acetate buffer having a sodium acetate concentration within the range of 5–25 mM, such as within the range of 10–20 mM, preferably about 15 mM. It is preferred that the pH of the sodium acetate buffer used for equilibration is within the range of 5.0 to 6.0, such as within the range of 5.4–5.9, preferably about 5.7. The conductivity is within the range of 1.0–1.4 mS/cm, preferably about 1.2 mS/cm. Suitable acetate buffers may be prepared from sodium acetate trihydrate and glacial acetic acid.

Prior to loading the clarified and optionally filtrated IgG-containing supernatant onto the ion exchange columns, the buffer concentration and pH of said supernatant are preferably adjusted, if necessary, to values substantially equivalent to the concentration and the pH of the employed equilibration buffer.

After loading the IgG-containing supernatant onto the columns in series, the columns are preferably washed (the initial washing) with one column volume of a washing buffer in order to ensure that the IgG-containing solution is quantitatively transferred from the anion exchange column to the cation exchange column. Subsequently, the anion exchange and the cation exchange columns are disconnected, and the cation exchange column is preferably washed in order to remove protein contaminants from the resin with a buffer having a pH and ionic strength sufficient to elute substantially all of the contaminants from the cation exchange resin without causing substantial elution of IgG.

The initial washing is advantageously performed by using the equilibration buffer, even though other buffers with a similar concentration and pH-value may be used for the washing. It is preferred that an acetate buffer is used for washing out contaminants from the cation exchange resin. The pH of the buffer could be from 5.0 to 6.0, such as within the range of 5.2–5.8, such as about 5.4.

The elution of the IgG from the cation exchange resin is preferably performed with a substantially non-denaturating buffer having a pH and ionic strength sufficient to cause efficient elution of the IgG, thereby recovering an IgG-containing eluate. In this context, efficient elution means that at least 75%, such as at least 80%, e.g. at least 85%, of the IgG proteins loaded onto the anion and cation exchange resins in series are eluted from the cation exchange resin. The elution is advantageously carried out as a gradient elution step. In the process of the present invention, the preferred buffer used is sodium acetate having a pH within the range of 5.0–6.0, such as 5.2–5.8, preferably about 5.4, and a concentration within the range of 5–40 mM, such as within the range of 10–25 mM, preferably about 15 mM.

It is preferred that the salt concentration of the eluting buffer is sufficiently high to displace the IgG from the resin. However, it is contemplated that an increase in pH and a lower salt concentration can be used to elute the IgG from the resin. In a preferred embodiment of the present process, the elution is conducted as a continuous salt gradient elution with sodium chloride concentrations within the range of 50–500 mM, preferably from about 125 mM to about 350 mM sodium chloride.

The elution can also be performed by step gradient elution. It is contemplated that the elution could also be performed as a constant salt elution, in which the elution buffer applied to the cation exchange column has only one single salt concentration in contrast to the gradient elution. If a constant salt elution is performed, the concentration of salt may advantageously be within the range of from about 350 mM to about 500 mM sodium chloride. The advantage of the gradient elution compared to the constant salt elution is that the elution is more effective with a salt gradient, but another advantage is that the eluate has a lower ionic strength which is advantageous because a high ionic strength is critical to the stability of IgG. The elution buffer may further comprise a protein stabilizing agent such as those mentioned below. Various other suitable buffer systems may be used for eluting the IgG, as will be appreciated by those skilled in the art.

Preferably, at least one protein stabilizing agent is applied to the IgG fraction immediately after or during the elution. Protein stabilizing agents are known to those skilled in the art and include e.g. different sugar alcohols and saccharides (such as sorbitol, mannose, glucose, trehalose, maltose), proteins (such as albumin), amino acids (such as lysine, glycine) and organic agents (such as PEG). Advantageously, the intermediary stabilizer chosen may be one that can be removed from the IgG-containing solution in the subsequent steps.

The suitable concentration of the protein stabilizing agent in the IgG-containing solution depends on the specific agent employed. In one preferred embodiment, the stabilizing agent is sorbitol, preferably at a final concentration within the range of 2–15% (w/v) sorbitol, e.g. about 2.5%.

Subsequent to elution from the cation exchange column, the eluate is preferably desalinated (i.e. dialysed) and advantageously concentrated. The change of buffer and the concentration of IgG can be performed by a combined dia/ultrafiltration process. The term "dia/ultrafiltration" means that the dialysis and concentration by diafiltration and ultrafiltration, respectively, are performed in one step. It is contemplated that the diafiltration and ultrafiltration may be performed as two separate steps. However, in order to prevent unnecessary loss of the product, it is presently preferred to perform the dialysis and concentration by the methods of diafiltration and ultrafiltration in one step.

The membranes employed for the dia/ultrafiltration advantageously have a nominal weight cutoff within the range of 10,000–100,000 Da. A preferred membrane type for the present process is a polysulfone membrane with a nominal weight cutoff of 30,000 Da, obtained from Millipore. Other ultrafiltration membranes of comparable material and porosity may be employed.

The extent of concentration may vary considerably. The solution is concentrated from about 10 g/l IgG to about 100 g/l, preferably to about 50 g/l. Following the concentration, the IgG concentrate is advantageously dialysed against a buffer with low ionic strength. Besides removing salt ions, this step also removes contaminants of low molecular weight from the solution and provides a means for buffer exchange for the next purification step. A preferred buffer for the diafiltration is 15 mM sodium acetate, pH 5.4 containing 2.5% (w/v) sorbitol. The exchange of buffer is continued until the conductivity of the ultrafiltrated solution is reduced to a value less than about 1.5 mS/cm, preferably less than about 1.3 mS/cm. During the dia/ultrafiltration, the pH is preferably kept within the range of 4.0–6.0, preferably 5.1–5.7, most preferably at about 5.4.

After dia/ultrafiltration, the concentration of the protein stabilizing agent is advantageously adjusted in the solution, if necessary, to the final optimal concentration characteristic for the specific protein stabilizing agent employed. If sorbitol is used, the sorbitol concentration is preferably adjusted to about 10% by weight.

It is preferred that the stabilized solution is filtered with a filter with a pore diameter within the range of 0.2–1.0 $\mu$m, preferably about 0.45 $\mu$m, in order to remove aggregates before the next step. At this stage the IgG-containing solution appears as a clear solution of an appropriate volume with a high stability as a combined result of the high purity, the low ionic strength, the acidic pH, the relatively high concentration of IgG and the stabilizer added.

In the production process of the IVIG product, at least two defined and validated virus removal and inactivation steps are presently incorporated, these steps preferably being precipitation with PEG as a general virus-removal step and an S/D treatment as a virus-inactivating step towards lipid enveloped viruses. Besides the stringent requirements to virus safety of the starting material, according to international guidelines, and the well known virus reducing capacity of a multistep purification process, the incorporation of two independent virus reduction steps being active against both enveloped and non-enveloped viruses, the medicament of the present invention is substantially virus-safe.

Infectious lipid enveloped viruses that may still be present in the IgG-containing solution are preferably inactivated at this stage of the process by addition of a virucidal amount of virus-inactivating agent to the IgG-containing solution. A "virucidal amount" of virus-inactivating agent is intended to denote an amount giving rise to a solution in which the virus particles are rendered substantially non-infectious and by this a "virus-safe IgG-containing solution" as defined in the art. Such "virucidal amount" will depend on the virus-inactivating agent employed as well as the conditions such as incubation time, pH, temperature, content of lipids, and protein concentration.

The term "virus-inactivating agent" is intended to denote such an agent or a method which can be used in order to inactivate lipid enveloped viruses as well as non-lipid enveloped viruses. The term "virus-inactivating agent" is to be understood as encompassing both a combination of such agents and/or methods, whenever that is appropriate, as well as only one type of such -agent or method.

Preferred virus-inactivating agents are detergents and/or solvents, most preferably detergent-solvent mixtures. It is to be understood that the virus inactivating agent is optionally a mixture of one or more detergents with one or more solvents. Solvent/detergent (S/D) treatment is a widely used step for inactivating lipid enveloped viruses (e.g. HIV1 and HIV2, hepatitis type C and non A-B-C, HTLV 1 and 2, the herpes virus family, including CMV and Epstein Barr virus) in blood products. A wide variety of detergents and solvents can be used for virus inactivation. The detergent may be selected from the group consisting of non-ionic and ionic detergents and is selected to be substantially non-denaturing. Preferably, a non-ionic detergent is used as it facilitates the subsequent elimination of the detergent from the IgG preparation by the subsequent step. Suitable detergents are described, e.g. by Shanbrom et al., in U.S. Pat. No. 4,314, 997, and U.S. Pat. No. 4,315,919. Preferred detergents are those sold under the trademarks Triton X-100 and Tween 80. Preferred solvents for use in virus-inactivating agents are di- or trialkylphosphates as described e.g. by Neurath and Horowitz in U.S. Pat. No. 4,764,369. A preferred solvent is tri(n-butyl)phosphate (TNBP). An especially preferred virus-inactivating agent for the practice of the present invention is a mixture of TNBP and Tween 80, but, alternatively, other combinations can be used. The preferred mixture is added in such a volume that the concentration of TNBP in the IgG-containing solution is within the range of 0.2–0.6% by weight, preferably at a concentration of about 0.3% by weight. The concentration of Tween 80 in the IgG-containing solution is within the range of 0.8–1.5% by weight, preferably at a concentration of about 1% by weight.

The virus-inactivation step is conducted under conditions inactivating enveloped viruses resulting in a substantially virus-safe IgG-containing solution. In general, such conditions include a temperature of 4–30° C., such as 19–28° C., 23–27° C., preferably about 25° C., and an incubation time found to be effective by validation studies. Generally, an incubation time of 1–24 hours is sufficient, preferably 4–12 hours, such as about 6 hours, to ensure sufficient virus inactivation. However, the appropriate conditions (temperature and incubation times) depend on the virus-inactivating agent employed, pH, and the protein concentration and lipid content of the solution.

It is contemplated that other methods for removal of or inactivating virus can also be employed to produce a virus-safe product, such as the addition of methylene blue with subsequent inactivation by radiation with ultraviolet light or nanofiltration.

After the solvent/detergent treatment, the solution is advantageously diluted with buffer. Optionally, the substantially virus-safe IgG-containing solution is filtered, preferably through a depth filter as described previously in an earlier step of the present process and/or through a sterile filter.

After virus-inactivation and preferably filtration, ion exchange chromatography is performed in order to remove the virus-inactivating agent and protein contaminants. This step is preferably performed as already described for the previous ion-exchange chromatography step in the present process, with the exceptions that the volume of the anion exchange resin is about half that of the cation exchange resin and that the washing before elution of IgG is more extensive, at least six column volumes of buffer are used. Additionally, in a preferred embodiment of the invention, the equilibration buffer is sodium acetate with a concentration within the range of about 5–25 mM, preferably 15 mM, and a pH within the range of about 5.0–5.8, preferably 5.4. As mentioned previously, the sodium acetate content and the pH of the IgG-containing solution are preferably adjusted to the same concentration and pH as the equilibration buffer. Additionally, in a preferred embodiment of the invention, a protein stabilizing agent, preferably maltose, is added to the recovered eluate to a final concentration within the range of 1–5%, preferably about 2.5% by weight.

The preferred method of eliminating the virus-inactivating agent is by ion exchange chromatography. However, other methods, such as oil extraction and alternative chromatographic methods, are contemplated to be useful. The appropriate method depends on the virus-inactivating agent employed. Removal of solvent/detergent may thus be achieved by binding the IgG to a resin and, subsequently, a thorough washing out of the inactivating agent with buffer. Cation exchange chromatography is a usable method. In a preferred embodiment of the present invention, anion exchange chromatography is also performed in addition to the cation exchange chromatography in order to improve the quality and overall purity of the final product of the present process.

After the ion exchange chromatography step, the IgG-containing eluate is preferably dialysed and concentrated; hereby the content of remaining smaller protein components is also effectively reduced. Advantageously, this can be performed by dia/ultrafiltration as described previously. The buffer employed for the diafiltration is sodium acetate, preferably at a concentration from about 4 to 10 mM, preferably 7.5 mM, and at a pH within the range from about 4.0 to 6.0, preferably about 5.1–5.7, such as about 5.4. Alternatively, other buffers such as sodium phosphate or acids can be used for the diafiltration. The diafiltration continues until the conductivity is less than or equal to 1 mS/cm. Optionally, the IgG-containing solution is further sterile filtered.

If desired, the purified IgG-containing solution which is substantially free from the virus-in-activating agent is subjected to further treatments for the purpose of making it suitable for formulation as a liquid product to be used e.g. intravenously, subcutaneously, or intramuscularly.

From a practical point of view it is preferred that the content of the liquid formulation of the immunoglobulin product is the same for storage as for use. The final concentration of IgG in the product is preferably within the range of 0.25–20% by weight (corresponding to 2.5–200 g of IgG/l), such as about 1–20% by weight, i.e. about 2%, 3%, 4%, 5%, 6%, 7%, 8%, 9%, 10%, 12%, 14%,16%, 18%.

It is known that a high protein concentration results in a higher stability of IgG. On the other hand, a high IgG concentration means that the maximum infusion rate when administering IgG intravenously to the patient has to be quite low as transfusion problems, due to the high osmotic pressure of the product, have to be avoided. A presently recommended concentration for intravenous administration by European Pharmacopoeia (Ph.Eur.) is 5% (w/v). On the other hand, a quite concentrated product (e.g. 10% or above) is advantageous for intramuscular or subcutaneous injections.

Although not preferred, it is evident that the products obtainable by the various process steps of the invention can also be used as e.g. freeze-dried products instead of as liquid formulations, although this is less favourable compared to the use of the immunoglobulin products as instant liquid formulations. The latter embodiment will be described in more detail in the following.

Liquid immunoglobulin products are most stable at an ionic strength markedly lower than that of plasma, i.e. the conductivity is preferably less than 1.0 mS/cm, preferably about 0.8 mS/cm.

The pH has an impact on the stability of IgG and on the infusion rate. Liquid immunoglobulin products are most stable under acidic conditions, i.e. below the isoelectric point of IgG, pH 6.4–8.5. The closer the pH value is to the physiological pH value (7.1–7.3), the higher infusion rate can be employed. As a consequence of the stability required, the pH of the immunoglobulin product of the invention will preferably be within the range of 5.1–5.7, such as between 5.2 and 5.6, such as about 5.4.

Furthermore, the immunoglobulin product may comprise protein stabilizing agents as described previously. In addition to sugar alcohols and saccharides (such as sorbitol, mannose, glucose, trehalose, maltose), also proteins (such as albumin), amino acids (such as lysine, glycine) and organic agents (such as PEG and Tween 80) may be used as well as stabilizers. The suitable concentration of the stabilizing agent in the IgG-containing solution depends on the specific agent employed as described previously.

The purified IgG solution is adjusted if necessary in order to obtain a stable and isotonic solution. The term "isotonic solution" is intended to denote that the solution has the same osmotic pressure as in plasma. As mentioned above, the ionic strength is markedly lower in the immunoglobulin product of the invention as a liquid formulation than in plasma. For that reason it is preferred that mono- or disaccharides are used to increase the osmolality of the solution since this does not affect the ionic strength. In a preferred embodiment of the present invention, maltose is added at a concentration ensuring that the solution is isotonic and, at the same time, maltose functions as an immunoglobulin-stabilizing agent. This is preferably performed by addition of maltose to a final concentration within the range of about 5% to 15% (w/v), preferably 10% (w/v); other saccharides, such as mannose and glucose, can alternatively be used.

The preferred final conditions for the immunoglobulin product are a compromise between stability and physiologically acceptable conditions with respect to e.g. pH, ionic strength and tonicity. Furthermore, the immunoglobulin product has to comply with the requirements of quality control tests, as specified in Monograph No. 918, Ph. Eur., 1997.

The main advantages of the product obtainable by the method of the invention are that, when formulated as a liquid preparation, the product is a combination of a liquid, ready-for-use product which, at the same time, is very stable, highly purified, has a largely normal distribution of IgG subclasses and has an extremely low IgA content as well as a low IgM content, and retained antibody activity and biological activity shown by the Fc function.

Moreover, it contains essentially no aggregates of immunoglobulins and/or other plasma proteins measured as polymers higher than dimers and has a low anticomplementary activity, and it has a very high content of IgG monomers and dimers. Monomeric IgG constitues at least 90%, which is considered to be ideal. Due to the high stability it is possible to avoid the addition of other stabilizers, such as albumin, glycine, detergent, or PEG. Finally, the product is virus-safe as the process comprises well-defined and validated virus-reduction steps aimed at removing and/or inactivating both lipid enveloped and non-lipid enveloped viruses.

The aim of validating a production step as a virus reduction step is to provide evidence that the production process will effectively inactivate/remove viruses which are either known to contaminate the starting materials, or which could conceivably do so. Validation studies involve the deliberate addition of a virus prior to the production steps to be validated and measuring the extent of its removal/inactivation after the production step or steps. GMP restraints prevent the deliberate introduction of any virus into the production facilities. Therefore, the validation should be conducted in a separate laboratory equipped for virological work on a scaled-down version of the production step and performed by staff with virological expertise in conjunction with the production engineers. The amount of virus added to the starting material for the production step which is to be validated should be as high as possible in order to determine the capacity of the production step to inactivate/remove viruses adequately. However, the virus spike should be added such that the composition of the production material is not significantly altered. Preferably the volume of the virus spike will be equal to or less than 10%.

Quantitative infectivity assays should be performed according to the principles of GLP and may involve plaque formation, detection of other cytopathic effects such as syncytia or foci formation, end point titration (eg., $TCID_{50}$ assays), detection of virus antigen synthesis or other methods. The method should have adequate sensitivity and reproducibility and should be performed with sufficient replicates and controls to ensure adequate statistical accuracy of the results.

Typically, a process step is challenged with 6 logs of virus, and if a reduction in the order of 4 logs or more is acquired, it is indicative of a clear effect with the particular test virus under investigation. Similarly, a reduction in the order of 4.5 logs, 5 logs, or even 5.5 logs, is indicative of a clear effect with the particular test virus under investigation, and the step can be classified as a validated virus reduction step The virus validation studies should be performed with viruses resembling those which may contaminate the product as closely as possible and secondly to represent as wide a range of physico-chemical properties as possible in order to test the ability of the system to eliminate viruses in general.

The virus validation studies should be performed in accordance with the CPMP Note for Guidance on Virus Validation Studies: The Design, Contribution and Interpretation of Studies Validating the Inactivation and Removal of Viruses (CPMP/BWP/268/95) and Note for Guidance on Plasma Derived Medicinal Products (CPMP/BWP/269/95).

The validation studies of the present process are presented in example 5.

The product of the invention is more than 95% pure, preferably above 98%. The high degree of purity is, inter alia, due to the fact that the product of the invention is obtained by at least one, preferably two, optionally serially connected anion-cation exchange chromatography steps. It is noteworthy in this context that it has been possible to obtain a high yield in spite of the number of process steps employed, in production scale of at least 3.5 g of IgG protein per kg of fresh frozen plasma.

The comparative studies which have been carried out (Example 2) have shown that the immunoglobulin product obtainable by the process of the invention has ideal functional properties, such as prominent antigen binding activities and a high Fc function. The presently preferred medicament developed by the present inventors is a 5% by weight immunoglobulin solution. Stability tests have so far indicated stability at 4° C. storage for more than one year, i.e. that the immunoglobulin product is devoid of aggregate formation or fragmentation of immunoglobulins G, loss of the desired biological activity, or increase of undesired activities, e.g. anticomplementary activity and prekallikrein activity as measured in vitro.

Based on the present invention, it is possible to obtain an IgG product that is more than 95%, such as at least 96%, or at least 97%, e.g. at least 98%, preferably at least 99%, more preferably at least 99.5% pure. The IgG product should contain less than 6 mg of IgA/I, such as less than 4 mg of IgA/I, preferably less than 3 mg of IgA/I, more preferably less than 2 mg of IgA/I.

It should be stressed that other products contain stabilizers in the form of a detergent, PEG, or albumin. In a preferred embodiment, the product of the present invention does not contain any of said stabilizers, instead a well-tolerated saccharide has been chosen.

The product of the present invention has, as one of its characteristics, a very low content of polymers and aggregates. In a preferred embodiment, the product of the present invention contains less than 1.5% polymers and aggregates, such as less than 1%, e.g. less than 0.5%, or less than 0.25% polymers and aggregates. The content of IgG monomers and dimers is at least 95%, such as at least 96%, or at least 97%, e.g. at least 98%, preferably at least 98.5%, or 99%. The content of monomeric IgG is at least 90% in the product.

Trials have shown clinical effect of the product of the present invention comparable to registered IVIG products. The product has been well-tolerated by the patients, and the turnover time of the immunoglobulins in circulation has been determined to be four weeks. In the present trials, the immunomodulating effect of IVIG, SSI has been shown to be convincing (data are presented in example 3).

The indications for IVIG are primary hypo/ agammaglobulinaemia including common variable immunodeficiency, Wiskott-Aldrich syndrome and severe combined immunodeficiency (SCID), secondary hypo/ agammaglobulinaemia in patients with chronic lymphatic leukaemia (CLL) and multiple myeloma, children with AIDS and bacterial infections, acute and chronic idiopathic thrombocytopenic purpura (ITP), allogenic bone marrow transplantation (BMT), Kawasaki's disease, and Guillan-Barré's syndrome. Neurology: Chronic inflammatory demyelinating polyneuropathy (CIDP), multifocal motoric neuropathy, multiple sclerosis, Myasthenia Gravis, Eaton-Lambert's syndrome, Opticus Neuritis, epilepsy.
Gynaecology: Abortus habitualis, primary antiphospholipid syndrome.
Rheumatology: Rheumatoid arthritis, systemic lupus erythematosus, systemic scleroderma, vasculitis, Wegner's granulomatosis, Sjöbgren's syndrome, juvenile rheumatoid arthritis.
Haematology: Autoimmune neutropenia, autoimmune haemolytic anaemia, neutropenia.
Gastrointestinal: Crohn's disease, colitic ulcerous, coeliac disease.
Others: Asthma, septic shock syndrome, chronic fatigue syndrome, psoriasis, toxic shock syndrome, diabetes, sinuitis, dilated cardiomyopathy, endocarditis, atherosclerosis, adults with AIDS and bacterial infections.

Apart from the mentioned indications for treatment with IVIG products, several severe autoimmune diseases, which commonly respond to cortico-steroid and immunosuppressive therapy, are considered target conditions for therapy with the product of the present invention. Among these are several neurological diseases such as polyradiculitis, and some immune-mediated peripheral polyneuropathies, but also some chronic inflammatory rheumatic and vascular conditions such as systemic vasculitis involving small vessels, polymyositis, and others.

A different mode of action of the product of the present invention may be the elimination of infectious antigens in chronic infections and an increase of IgG metabolism.

The invention is further illustrated by the following examples, which are not intended to be limiting.

EXAMPLES

Example 1
Process Steps in the Purfication of Immunoglobulin (with the exception of step 5, all steps are carried out at 5±3° C.)
Step 1: Preparation of Cohn Fraction II+III Paste Cohn fraction II+III paste is prepared from human plasma by the standard Cohn-fractionation method (Cohn E., et al., (1946) J Am Chem Soc, 459–475) essentially as modified by Kistler-Nitschmann (Kistler P and Nitschmann HS, (1952), Vox Sang, 7, 414–424). The ethanol precipitation is initiated after the cryoprecipitate has been removed and, if desired, after adsorption of certain plasma proteins (such as Factor IX and Antithrombin) to e.g. an ion exchange material and/or a Heparin Sepharose® matrix.

The exact conditions (pH, ethanol concentration, temperature, protein concentration) for obtaining the fraction II–III paste appear from the figure at page 266 in Harns JR (ed), Blood Separation and Plasma Fractionation, Wiley-Liss, New York, 1991. The paste is isolated on a filter press by adding filter aid prior to filtration.
Step 2: Extraction of Immunoglobulins from Cohn Fraction II+Ill Paste From 140 kg of fraction II+III paste including 30 kg of filter aid (Schenk, Germany) (corresponding to a starting volume of plasma of about 1150 kg), extraction is accomplished by first adding 525 kg of 2.33 mM sodium phosphate/acetate buffer, pH 4.0, with slow stirring for about 1.5 hours, followed by 2 consecutive additions of 350 kg of water for injection (WFI) with stirring for about 1.5 hours after each addition. Finally, about 280 kg of 21.5 mM sodium phosphate/acetate, pH 7.0, are added, thereby adjusting the pH of the suspension to 5.4.

The suspension is filtered through a depth filter (C-150AF, Schenk, Germany). The filtrate contains, among other proteins, the immunoglobulins.
Step 3: Precipitation of Protein Aggregates and Removal of Virus by PEG 6000

PEG 6000 (Merck, Germany) is added to the filtrate of step 2 to a final concentration of 6% by weight. After precipitation for 4 hours, the PEG suspension is centrifuged to clarity in a flow-through centrifuge (Westfalia BKA28, Germany) and is depth filtered (50LA and 90LA, Cuno, France) and subsequently sterile filtered through a 0.22 μm filter (Durapore, Millipore, U.S.A.). The filtered PEG supernatant is buffer-adjusted by adding 1 part of a 0.45 M sodium acetate buffer, pH 5.7, to 29 parts of supernatant to reach a pH of 5.7.
Step 4: Purification by Serial Anion and Cation Exchange Chromatography (I)

Two chromatography columns are packed with 56 l of DEAE Sepharose FF®(Pharmacia Biotech, Sweden) and 56 l of CM Sepharose FF® (Pharmacia Biotech, Sweden), respectively. The columns are connected in series so that the liquid flow first passes through the DEAE Sepharose resin and, subsequently, through the CM Sepharose resin. The column resins are equilibrated with 15 mM sodium acetate buffer, pH 5.7. Then, the solution from step 3 is applied to the two columns in series.

During the ion exchange chromatography, most contaminating proteins in the applied solution bind to the DEAE Sepharose resin. Whereas IgG runs through without binding to the DEAE Sepharose resin, IgG binds to the CM Sepharose resin when the solution migrates through it. After application of the solution, and washing with one column volume of equilibration buffer, the DEAE column is disconnected from the CM column. Then the CM column is washed with three column volumes of 15 mM sodium acetate buffer, pH 5.4, then IgG is eluted with a gradient of NaCl from 125 mM to 350 mM NaCl, 15 mM sodium acetate, pH 5.4. The eluted IgG fraction is collected in sorbitol to a final concentration of 2.5% by weight.
Step 5: Solvent/Detergent (S/D) Treatment of the IgG Fraction The eluted IgG fraction is concentrated and desalted by ultra/diafiltration to a concentration of approximately 50 g of IgG/litre. The employed membrane is a polysulfone membrane, nominal weight cutoff of 30 kDa (Millipore). The diafiltration is performed against a buffer of 15 mM sodium acetate, pH 5.4, containing 2.5% by weight of sorbitol and is continued until the conductivity is less than 1.4 mS/cm. The IgG content of the solution is determined spectrophotometrically by measuring at 280 nm ($A_{280}$). The sorbitol concentration is adjusted to 10% by weight and the solution is filtered through a 0.45 μm filter (Pall Corporation, UK). Tween 80 and TNBP are then added to a final concentration of 1% and 0.3% by weight, respectively, for subsequent S/D treatment. The S/D treatment proceeds for at least 6 hours at 25° C.

Step 6: Removal of S/D by Ion Exchange Chromatography (II)

Two serially connected columns packed with 28 l of DEAE and 56 l of CM Sepharose FF, respectively, are equilibrated with 15 mM sodium acetate, pH 5.4. The S/D-treated IgG fraction from step 5 is diluted with 5 parts of 15 mM acetate buffer, pH 5.4, filtered through a depth filter (Cuno 90 LA) and subsequently sterile filtered (Sartobran, Sartorius), and applied to the two columns connected in series. The ion exchange chromatography and the subsequent elution of IgG from the CM column are carried out essentially as described in step 4, except that the CM column is extensively washed with 6 column volumes of buffer to remove agents from the S/D treatment. The eluted IgG fraction is collected in maltose (Merck, Germany) to a final concentration of 2.5% by weight.

Step 7: Final Concentration and Formulation of Immunoglobulin for Intravenous Use The eluted IgG fraction from step 6 is subjected to ultrafiltration and desalting by diafiltration against 7.5 mM sodium acetate containing 2.5% by weight of maltose, pH 5.4 to a final conductivity of less than 1 mS/cm. The employed membrane is a polysulfone membrane with a 100 kDa nominal weight cutoff allowing proteins with lower molecular weight to be eliminated. The final concentration of IgG is adjusted to 50 g/litre, and the maltose is adjusted to a final concentration of 10% (w/v). The maltose-adjusted final preparation is filtered through a sterile filter (Sartopure GF 2, Sartorius), and filled aseptically.

Example 2

Results From An Analytical Study Of A Product Obtained By The Present Process, Compared To Other IVIG Products

| Error! Bookmark not defined. | Gammonativ lyophilized | Octagam liquid | Gammagard lyophilized | IVIG, SSI liquid |
|---|---|---|---|---|
| Purity | 45.4%[1] | 99.1% | 94.6%[1] | 99.8% |
| Albumin | 50 mg/ml[2] | small amounts | 3 mg/ml[2] | not detectable |
| Content of monomers + dimers | 98.3%[3] | 96.8% | 97.6%[3] | 99.3% |
| polymers + aggreg | 0.8%[3] | 1.6% | <0.1% | |
| ACA | 26% | 30% | 34% | 32% |
| PKA | <8.5 IE/ml | <8.5 IE/ml | <8.5 IE/ml | <8.5 IE/ml |
| Haemaglutinin, 3% solution | | | | |
| anti-A > 1:2 | negative | negative | negative | negative |
| anti-B > 1:2 | negative | negative | negative | negative |
| Fc function | 169% | 121% | 132% | 178% |
| Subclass distribution | | | | |
| IgG1 | 60.0% | 61.9% | 67.7% | 56.6% |
| IgG2 | 35.8% | 33.1% | 27.2% | 39.4% |
| IgG3 | 3.5% | 3.6% | 4.4% | 2.6% |
| IgG4 | 0.7% | 1.4% | 0.6% | 1.5% |
| IgA | 2.96 mg/l | 54.7 mg/l | 0.85 mg/l | 1.36 mg/l |
| IgM | 0.28 mg/l | 39.1 mg/l | 0.99 mg/l | 0.16 mg/l |
| Tween 80 | <20 ppm | <20 ppm | not determined | <20 ppm |
| TNBP | 2.0 ppm | 1.5 ppm | 1.5 ppm | 1.5 ppm |
| PEG | 0.01 mg/ml | 0.01 mg/ml | 1.6 mg/ml[4] | 0.02 mg/ml |
| pH | 6.7 | 5.7 | 6.7 | 5.6 |
| Total protein concentration | 97 g/l | 45 g/l | 50 g/l | 51 g/l |
| Maltose or glucose | 20 mg/ml | 92 mg/ml | 15 mg/ml | 88 mg/ml |

[1]without correction for HSA; [2]declared by producer; [3]corrected for HSA peak; [4]used as a stabilizer Error! Bookmark not Defined.Purity (Protein Composition)

Pharmacopoeia purity requirements for an IVIG-preparation is at least 95% IgG, that is not more than 5% non-IgG-contaminating proteins present. Purity is regarded as being of very high importance for several reasons. From a rational point of view, only the protein which carries the desired function should be present, and other contaminating proteins may be potentially harmful, e.g. cause unwanted adverse effects and/or influence the stability of the product.

Purity can e.g. be analyzed by an electrophoretic technique as described in detail in Ph. Eur., 1997, pages 964–965, where proteins are separated in a cellulose acetate gel. For practical purposes, however, an agarose gel is used. After electrophoresis, the gel is fixed, dried, and stained. Protein bands are finally monitored by scanning. It appears from the table above that the product of the invention is virtually pure (99.8%).

Albumin

The albumin content was analyzed by crossed immunoelectrophoresis essentially as described by C. B. Laurell (Anal Biochem (1965),. 10, 358–361). 5 μl of product was analyzed against anti-human albumin antibodies (DAKO A/S, Denmark, No. A0001 (1/100)). Due to the high purity no albumin was detectable in the analyzed product of the invention.

Error! Bookmark not Defined.Content of IgG Monomers and DimersThe content of IgG monomers and dimers can be analyzed by gel permeation chromatography, and monitored from the chromatogram by integration of the areas of the monomer and of the dimer peak, cf. Ph.Eur. The results of the various analyses are listed in the table above from which it appears that the sum of the monomer + dimer areas constitutes 99.3% of the total area of the chromatogram (from this monomeric IgG constitutes 92%) for the product of the invention.

Content of Polymers and

The presence of polymers and aggregates is known to be the cause of serious adverse effects, often influenza-like symptoms. Because of the very high degree of purity reached by the rather gentle production process, the immunoglobulin product obtainable by the process of the invention is largely free of polymers and aggregates.

Polymers can be analyzed by gel permeation chromatography, and any protein peaks with retention times shorter than the retention time for dimeric IgG are considered polymeric as described in Ph.Eur.

According to Ph.Eur. and other guidelines, the content of protein aggregates should preferably be less than 3%. The product of the present process contains no measurable aggregates and is thus considered to contain less than 0.1% polymers and aggregates.

Anti-complementary Activity (ACA) and Prekallikrein Activator Activity (PKA)

ACA and PKA are measured as described in Ph.Eur.

ACA should preferably be as low as possible. According to Ph.Eur. the complement consumption should be less than or equal to 50%. The complement consumption of the measured sample of the product of the invention is about 30%, i.e. comparable to that of the other products analyzed. It should be noted that the presence of albumin tends to suppress complement consumption (inventor's observation).

PKA, if present in substantial amounts, is essential for the hypotensive adverse effect of the product. Therefore, PKA should preferably be as low as possible in an immunoglobulin product. According to Ph.Eur. it should be<35 1U/ml when measured as outlined in Ph.Eur. PKA of the product of invention as well as of the other products analyzed is less than the quantitation level of the method, i.e. below 8.5 lE/ml.

Haemagglutinins Error! Bookmark not Defined

The IgM fraction of plasma immunoglobulins comprises the haemagglutinins, that is antibodies against blood type A and B antigens. The presence of such antibodies may cause unwanted adverse effects due to a possible haemolytic reaction if the recipient carries blood types A and/or B.

According to Pharmacopoeia requirements, the content of haemagglutinins must be lower than that causing agglutination of A/B erythrocytes in a dilution 1:64 of the immunoglobulin product. All the products analyzed fulfil this requirement.

Fc-function

Retained antigen binding activities are essential for the biological functions of the IVIG. This is also true for the immunomodulating activities. On the other hand, a retained Fc-function is essential for the effect of IVIG on various phagocytic cells and activation of the complement system. Fc-function can be demonstrated using various techniques, but an accepted methodology described in Ph.Eur. measures the complement-activating potential of antibodies in the preparation against rubella antigen. Activity is compared to that of a biological reference preparation (BRP, Ph.Eur.) of immunoglobulins set to be 100%. The product complies with the test if the relative activity is more than 60% of the reference preparation. It appears that the Fc-function of the product of the invention is very well preserved, particularly in comparison with the other liquid product analyzed, most likely due to the gentle purification process.

Subclass Distribution

The distribution of IgG subclasses is measured by a standard Mancini immunodiffusion method essentially as described by A. Ingild (Scand J Immunol, (1983), 17, 41 Suppl. 10). The concentrations are determined by use of a WHO reference serum (67/97). It is required that the subclass distribution should be within the range of normal human plasma with median concentrations in the range of 3.7–10.2 g IgG1/l serum, 1.1–5.9 g IgG2/l serum, 0.15–1.3 g IgG3/l serum, and 0.06–1.9 g IgG4/l serum (R. Djurup et al. Scand J. Clin Lab Invest 48, 77–83). Thus, the subclass distribution of all the products is acceptable.

IgA-content

The presence of IgA is known to potentially cause sensibilisation of IgA-deficient recipients. If an IgA-deficient patient receives an IgA-containing immunoglobulin preparation, IgA may be considered as a foreign antigen, and the result may be the induction of antibodies against IgA in the recipient. The next time an IgA-containing preparation is infused to the patient, an anaphylactic reaction may be provoked. It is therefore essential that an immunoglobulin preparation contains as little IgA as possible. IgA in an IVIG product can be monitored using an ELISA-technique, e.g. where a polyclonal anti-IgA is used to capture IgA, and a labelled anti-IgA is used for the detection of bound IgA. Standards are constructed by dilutions of a calibrator (No. X908, DAKO A/S, Denmark) with a declared IgA-content.

The product of the process described in Example 1 contains less than 2 mg of IgA/l which is a considerably lower IgA-content than that of the other analyzed liquid product. The physico-chemical similarities between IgG and IgA make it difficult to separate these immunoglobulins during a purification process. However, the two anion/cation exchange chromatography steps in the process reduce the IgA-content to a very low level.

IgM-content

IgM in an Ig-preparation can be monitored using an ELISA-technique, e.g. where a polyclonal anti-IgM is used to capture IgM, and a labelled anti-IgM is used for detection. Standards are constructed by dilutions of a calibrator (No. X908, DAKO A/S, Denmark) with a declared IgM-content. It appears from the table that the IgM-content of the product of the invention is very low and markedly lower than that of the other liquid product.

Tween 80. TNBP and PEG80

Tween 80, TNBP and PEG are measured by standard procedures. In general, the content of these additives should be as low as possible.

pHError! Bookmark not Defined pH of the analyzed liquid products is acidic, pH 5.6–5.7, whereas the analyzed lyophilized products are neutral after dissolution, with a pH of 6.7.

Total Protein Concentration

According to Ph.Eur. the protein concentration should be at least 50 g/l ±10%; all the products fulfil this requirement. The protein concentration is measured by the method of Kjeldahl.

Maltose and Glucose Stabilizers

Saccharides are commonly used stabilizers of immunoglobulin products, they have good stabilizing properties and are quickly excreted. The content of maltose, sucrose, and glucose is determined by use of a commercial kit (Boehringer Mannheim, Germany) with maltose as a reference.

It appears that the two lyophilized products stabilized by albumin and albumin as well as PEG, respectively, also contain a saccharide stabilizer in concentrations from about 15 mg/ml to 20 mg/ml. The product of the invention and the other liquid product are very equally stabilized, i.e. with about 9%, 88 mg/ml and 92 mg/ml, of maltose. By regarding the content of polymers and aggregates as a parameter of stability, the product of the invention has a higher stability than the other liquid product analyzed, although their formulations appear very similar.

Example 3
Results From Clinical Trials

The clinical studies of the product of the present invention, also referred to as IVIG, SSI, are carried out in accordance with ICH and CPMP/388/95 guidelines.

Pharmacokinetics, effect and safety have been examined. The clinical trials have so far included four groups of patients: patients with primary immunodeficiency syndrome (15 patients), secondary immunodeficiency syndrome (6 patients), idiopathic thrombocytopenic purpura (15 patients) and patients with chronic inflammatory demyelinating polyneuropathia (5 patients).

Patients with primary immunodeficiency syndrome or secondary immunodeficiency syndrome were treated with 0.2–0.4 g/kg with intervals of 2–5 weeks. Patients with idiopathic thrombocytopenic purpura were treated with 400 mg/kg per day for five days or with 1000 mg/kg per day for two days.

For safety measures serum-transaminases, serum-creatinine and virus markers have been determined in all patients. Five patients with idiopathic thrombocytopenic purpura have been followed for virus, kidney and liver safety markes for up to a total of 24 weeks.

Pharmacokinetics $T_{1/2}$, was measured to 30,5 days (median). This is in accordance with results of other IVIG medicaments.

Effect

For patients with primary and secondary immunodeficiency syndrome, days lost through sickness, hospitalisations, days with antibiotics, days with fever and the number of pneumonias were registered retrospectively for a 6-month period during which the patients had been treated with other registered IVIG medicaments. In the following 6 months during which the patients were treated with Immunoglobulin SSI, liquid, the same parameters were registered.

The conclusion is that Immunoglobulin SSI, liquid is just as effective as other IVIG compositions for the prophylaxis/prevention of infections in patients with primary and secondary immunodeficiency syndrome.

In 80% of patients with idiopathic thrombocytopenic purpura, the number of platelets raised from $<30\times10^9/L$ before the treatment with Immunoglobulin SSI, liquid to $>50\times10^9/L$ after the treatment. The increase in the platelet count and the duration of the remission in the individual patient were on the same level as after administration of the same dose of other IVIG medicaments, in the cases where comparison was possible. One patient receiving IVIG for the first time was refractory to the test drug. Such a reaction to IVIG is not infrequent, and thus not surprising. Details of the rise of platelets and the duration of the rise are under way.

The conclusion is that Immunoglobulin SSI, liquid is just as effective as other IVIG medicaments in the treatment of low platelet count in patients with chronic idiopathic thrombogenic purpura.

According to clinicians, and patients suffering from chronic inflammatory demyelinating polyneuropathia, the IVIG, SSI has shown identical efficacy to the IVIG administrered prior to the trial. IVIG, SSI was tolerated by the patients equally well as other IVIG products were tolerated by the patients.

Safety

Apart from one severe adverse event, splenectomia assessed by the investigator to have no relation to test drug, only minor adverse events have been registered. These adverse effects were mainly headache fever, and vomiting. So far, there have been no reports on abnormal vital signs during infusions of IVIG, SSI. No viral seroconversions have been registered. There have been no reports on kidney or liver damages or cases of anaphylactic shocks.

The clinical studies show that Immunoglobulin SSI, liquid is well tolerated. The frequency of side effects, degree and species does not deviate from experiences with other IVIG medicaments.

Example 4
Results From Stability Study For IVIG Liquid

In order to test if the liquid IVIG product is stable over time, a Real time Real conditions study of stability was conducted. A total of 4 consecutive batches (250 ml of each sample) of the IVIG product were involved in the study and stored at between 2° C.–8° C. for at least 12 months. Samples from the four batches were analyzed at time zero, 6 month at storage and 12 months at storage. The results of the study are presented below as means of 4 batches.

|  | 0 months of storage | 6 months of storage | 12 months of storage |
|---|---|---|---|
| Appearance | Slightly opalescent and colourless | Slightly opalescent and colourless | Slightly opalescent and colourless |
| Content of monomers + dimers | 100% | 99.6% | 99.5% |
| polymers + aggreg | <0.1% | <0.1% | <0.1% |
| ACA | 39.7% | 38.2% | 37.3% |
| PKA | <8.5 IE/ml | <8.5 IE/ml | <8.5 IE/ml |
| Fc function | 107% | 113% | 111% |
| Subclass distribution |  |  |  |
| IgG1 | 59.2% | 57.7% | 57.1% |
| IgG2 | 36.4% | 38.1% | 38.6% |
| IgG3 | 2.7% | 2.6% | 2.5% |

-continued

| | 0 months of storage | 6 months of storage | 12 months of storage |
|---|---|---|---|
| IgG4 | 1.8% | 1.6% | 1.7% |
| pH | 5.5 | 5.5 | 5.5 |
| Protein composition (% IgG) | 99.8% | 99.7% | 99.1% |
| Total protein concentration | 48.8 g/l | 48.3 g/l | 49.2 g/l |
| Osmolality | 348 mOsm/kg | 347 mOsm/kg | 350 mOsm/kg |

All the above mentioned tests were carried out in accordance with Ph.Eur. and as described in Example 2.

The observation that the content of monomers and dimers is constant over a period of 12 months indicates that polymers are not formed in the sample. The presence of immunoglobulin polymers is known, among others, to be the cause of serious adverse effects, often influenza-like symptoms. Because of the very high stability of the immunoglobulin product obtainable by the process of the invention, the product is largely free of polymers and aggregates even after a long period of storage.

No increase in ACA is observed over time, although batches expressing rather high ACA deliberately have been included in this stability study. If an increase in ACA was observed, it might indicate that aggregates were being formed during storage. Thus, the constant ACA over time indicates that no aggregates are being formed.

The results further indicate that no prekallikrein activator activity has developed during storage of the product, as the PKA activity does not increase. It should be noted, however, that the values measured are below the lower quantification level.

The measure of Fc-function indicates that the presence of intact functional IgG is maintained during storage. Thus, no proteases are present in the samples, as they would have degraded the proteins and thereby lowered the Fc-function. Denaturation of IgG molecules has neither taken place as this would have decreased antigen binding activity.

As it will be known by the person skilled in the art, there might be difference in the stability of the various subclasses of IgG. As can be seen from the present results, all subclasses are maintained during storage indicating that the product is stable. This is further supported by the finding that the protein composition of IgG in the samples with approximately the same total protein concentration is almost unchanged over time, indicating that there is no overall degradation of IgG. i.e. the product of the present invention is stable and can be stored at least for 12 months at 2–8° C. without significant changes of characteristics, and by this efficacy and safety is demonstrated.

Example 5
Validated Virus Reduction Steps In The Present Process Of IVIG
Virus Removal By A Partitioning Step Precipitation of virus present in the immunoglublin solution by polyethylene glycol Virus validation studies have been performed employing two small non-enveloped viruses, the following virus reductions were obtained:
removal of 6.3 $\log_{10}$ of Hepatitis A Virus (HAV)
removal of 7.2 $\log_{10}$ of Polio Virus Virus validation studies have been performed employing two enveloped viruses, the following virus reductions were obtained:

removal of 7.6 $\log_{10}$ of HIV
removal of 7.5 $\log_{10}$ of BVDV

Virus Inactivation By A S/D Treatment Step

Treatment of the immunoglobulin solution with 1% Tween 80+0.3% TNBP, at 25° C. for>6 hours.

Virus validation studies have been performed employing four enveloped viruses, the following virus reductions were obtained:
inactivation of 7.4 $\log_{10}$ of HIV
inactivation of 5.3 $\log_{10}$ of Sindbis Virus
inactivation of 4.1 $\log_{10}$ of BVDV
inactivation of 5.1 $\log_{10}$ of PRV A total of 8 validation studies have been performed on two different steps in the process of the present invention. The PEG precipitation step has been validated as a virus removal step employing four different viruses, two small non-enveloped viruses HAV and Polio virus, and two enveloped viruses HIV and BVDV as model for Hepatitis C Virus. These studies showed that all four viruses were efficiently removed by PEG precipitation. The PEG precipitation step is therefore validated as an efficient virus removal step. The S/D treatment has validated employing four different enveloped viruses. From the data of the validation studies it appears that the S/D treatment step efficiently inactivated all four viruses. The S/D treatment step is therefore validated as an efficient virus inactivation step. Both virus reduction steps in the IVIG process, removal by PEG precipitation and inactivation by S/D treatment, have been validated efficiently to remove and inactivate four different viruses each. The cumulative reduction factors of HIV and BVDV in the process are 15 and 11.6, respectively. By this the product of the present process can be regarded as virus safe.

What is claimed is:

1. A process for purifying immunoglobulin, i.e., immunoglobulin G (IgG), from a crude immunoglobulin-containing plasma protein fraction, which process comprises the steps of:

(a) preparing an aqueous suspension of the crude immunoglobulin-containing plasma protein fraction;

(b) adding a water soluble, substantially non-denaturating protein precipitant to the said suspension of step (a) in an amount sufficient to cause precipitation of a high proportion of non-immunoglobulin G proteins, aggregated immunoglobulins and particles including potentially infectious particles, without causing substantial precipitation of monomeric immunoglobulin G, thereby forming a mixture of a solid precipitate and a liquid supernatant;

(c) recovering a clarified immunoglobulin G-containing supernatant from the mixture of step (b);

(d) applying the clarified immunoglobulin G-containing supernatant of step (c) to an anion exchange resin and subsequently a cation exchange resin;

(e) washing out protein contaminants and the protein precipitant from the cation exchange resin of step (d) with a buffer having a pH and ionic strength sufficient to remove the contaminants from the resin without causing substantial elution of immunoglobulin G;

(f) eluting immunoglobulin G from the cation exchange resin of step (e) with a substantially non-denaturing buffer having a pH and ionic strength sufficient to cause efficient elution of the immunoglobulin G, thereby recovering an immunoglobulin G-containing eluate;

(g) performing a dia/ultrafiltration on the immunoglobulin G-containing eluate of step (f) to concentrate and/or dialyse the eluate, and optionally adding a stabilizing agent, thereby forming a concentrated and/or dialysed and optionally stabilized product;

(h) adding a virucidal amount of virus-inactivating agent to the product of step (g) resulting in a substantially virus-safe immunoglobulin G-containing solution;

(i) applying the immunoglobulin G-containing solution of step (h) to an anion exchange resin and subsequently to a cation exchange resin;

(j) washing the cation exchange resin of step (i) with a buffer having a pH and ionic strength sufficient to wash out protein contaminants and the virus-inactivating agent from the resin without causing substantial elution of immunoglobulin G;

(k) eluting immunoglobulin G from the cation exchange resin of step (j) with a substantially non-denaturing buffer having a pH and ionic strength sufficient to cause efficient elution of the immunoglobulin G, thereby recovering an immunoglobulin G-containing eluate; and (l) subjecting the immunoglobulin G-containing eluate of step (k) to dia/ultrafiltration to lower the ionic strength and concentrate immunoglobulin G of the solution, and adjusting the osmolality by adding a saccharide.

2. The process according to claim 1, wherein the immunoglobulin G-containing plasma protein fraction is selected from the group consisting of Cohn fraction II; Cohn fractions II and III; and Cohn fractions I, II and III.

3. The process according to claim 1, wherein the suspension in step (a) is maintained at a temperature from 0° C. to 12° C. and the suspension in step (a) is maintained at a pH below 6.

4. The process according to claim 1, wherein the protein precipitant in step (b) is selected from the group consisting of polyethylene glycol (PEG), caprylic acid, and ammonium sulphate.

5. The process according to claim 4, wherein the protein precipitant is PEG having a molecular weight within the range 3000–8000 Da.

6. The process according to claim 5, wherein said PEG is a number selected from the group consisting of PEG 3350, PEG 4000, PEG 5,000, and PEG 6,000.

7. The process according to claim 1, wherein the anion exchange resin and the cation exchange resin in step (d) and/or step (i) are connected in series.

8. The process according to claim 7, wherein the buffer used for the anion exchange chromatography and the cation exchange chromatography is the same buffer, and the pH of said same buffer is below 6.0.

9. The process according to claim 1, wherein the anion exchange resin in step (d) and/or step (i) contains diethylaminoethyl groups and/or the cation exchange resin in step (d) and/or step (i) contains carboxymethyl groups.

10. The process according to claim 1, wherein the buffer used throughout steps (b) to (I) is an acetate buffer.

11. The process according to claim 10, wherein said acetate buffer has a pH of 5.0–6.0 and a molarity of 5–25 mM.

12. The process according to claim 1, wherein the virus-inactivating agent in step (h) is a mixture of at least one non-ionic or ionic detergent and at least one solvent.

13. The process according to claim 1, wherein the virus-inactivating agent in step (h) is a mixture of at least one substantially non-denaturing detergent and at least one tri(lower alkyl) phosphate solvent.

14. The process according to claim 1 wherein said potentially infectious particles are virus particles.

\* \* \* \* \*